United States Patent [19]

Itatani et al.

[11] 4,048,197

[45] Sept. 13, 1977

[54] 2,3,3',4'-BIPHENYLTETRACARBOXYLIC ACID DIANHYDRIDE

[75] Inventors: Hiroshi Itatani; Mikito Kashima; Masaoki Matsuda; Hataaki Yoshimoto; Hiroyuki Yamamoto, all of Ichihara, Japan

[73] Assignee: UBE Industries, Ltd., Ube, Japan

[21] Appl. No.: 597,789

[22] Filed: July 21, 1975

Related U.S. Application Data

[62] Division of Ser. No. 324,050, Jan. 19, 1973, Pat. No. 3,940,426.

[30] Foreign Application Priority Data

Apr. 3, 1972 Japan .................................. 47-32554
May 19, 1972 Japan .................................. 47-49143

[51] Int. Cl.$^2$ ..................................... C07D 307/89
[52] U.S. Cl. ......................................... 260/346.3
[58] Field of Search ................................. 260/346.3

[56] References Cited

FOREIGN PATENT DOCUMENTS 2,036,876  2/1971  Germany

OTHER PUBLICATIONS

Kenner et al., J. Chem. Soc., V. 105, pp. 2471-2482 (1914).
Itatani et al., Chem. and Industry, June 12, 1971, pp. 674-675.
Cram et al., Organic Chem.-McGraw Hill, p. 305 (1959).

*Primary Examiner*—Henry R. Jiles
*Assistant Examiner*—Bernard Dentz
*Attorney, Agent, or Firm*—Sughrue, Rothwell, Mion, Zinn & Macpeak

[57] ABSTRACT

A process for separating and purifying biphenyltetracarboxylic dianhydride isomers from a mixture of these isomers by fractional crystallization in aliphatic acid anhydrides or acetone. The isomeric mixture is obtained by heating biphenyltetracarboxylic acids, optionally in the presence of an aliphatic acid anhydride. The biphenyltetracarboxylic acids are obtained by oxidizing coupling dimers of o-xylene or by hydrolyzing coupling dimers of dimethyl phthalate. 2,3,3',4'-biphenyltetracarboxylic acid dianhydride which can be isolated from the above mixture can be used to form polyimide.

1 Claim, No Drawings

2,3,3',4'-BIPHENYLTETRACARBOXYLIC ACID DIANHYDRIDE

This is a division of application Ser. No. 324,050, filed Jan. 19, 1973 now U.S. Pat. No. 3,940,426.

THE INVENTION

The claimed invention is 2,3,3',4'-biphenyltetracarboxylic acid dianhydride.

The synthesis and utility of this compound are described in applicants U.S. Pat. No. 3,940,426, issued Feb. 24, 1976 (Class 260, subclass 346.3), which matured from application Ser. No. 324,050, of which this application is a division. See Example 23 of said U.S. patent for a method of synthesis and see column 4, lines 34–38 of said U.S. patent for the utility of this compound.

What we claim is:

1. 2,3,3',4'-Biphenyltetracarboxylic acid dianhydride.